(12) United States Patent
Nieuwkamp

(10) Patent No.: US 6,779,380 B1
(45) Date of Patent: Aug. 24, 2004

(54) MEASURING SYSTEM FOR THE CONTROL OF RESIDUAL DUST IN SAFETY VACUUM CLEANERS

(75) Inventor: Wolfgang Nieuwkamp, Senden (DE)

(73) Assignee: WAP Reinigungssysteme GmbH & Co., Bellenberg (DE)

( * ) Notice: Subject to any disclaimer, the term of this patent is extended or adjusted under 35 U.S.C. 154(b) by 0 days.

(21) Appl. No.: 09/869,614

(22) PCT Filed: Dec. 10, 1999

(86) PCT No.: PCT/EP99/09728
§ 371 (c)(1),
(2), (4) Date: Aug. 7, 2001

(87) PCT Pub. No.: WO00/40136
PCT Pub. Date: Jul. 13, 2000

(30) Foreign Application Priority Data

Jan. 8, 1999 (DE) .......................... 199 00 484

(51) Int. Cl.[7] .............................. G01N 30/64; B03C 3/00
(52) U.S. Cl. .................... 73/28.01; 73/28.04; 73/28.05; 15/339
(58) Field of Search ............................ 73/28.01, 28.04, 73/28.05, 53.01, 53.04, 54.11, 54.14, 61.71, 61.73, 64.48

(56) References Cited

U.S. PATENT DOCUMENTS

| | | | | |
|---|---|---|---|---|
| 3,674,316 A | * | 7/1972 | De brey | 406/35 |
| 4,077,782 A | * | 3/1978 | Drummond et al. | 96/80 |
| 4,175,892 A | * | 11/1979 | De brey | 406/35 |
| 4,323,946 A | * | 4/1982 | Traux | 361/218 |
| 4,375,673 A | * | 3/1983 | Lewis et al. | 702/29 |
| 4,531,486 A | * | 7/1985 | Reif et al. | 123/198 DC |
| 4,601,082 A | * | 7/1986 | Kurz | 15/319 |
| 4,607,228 A | | 8/1986 | Reif | 324/454 |
| 4,904,944 A | * | 2/1990 | Dechene et al. | 324/454 |
| 5,054,325 A | * | 10/1991 | Dechene et al. | 73/861.04 |

(List continued on next page.)

FOREIGN PATENT DOCUMENTS

| | | | |
|---|---|---|---|
| AU | 2001798 | * 10/2001 | G01N/15/06 |
| DE | G 92 09 407.4 | 9/1992 | |
| DE | 197 29 144 | 2/1999 | |
| EP | 0 693 178 | 3/1994 | |
| EP | 0 890 834 | 7/1998 | |

(List continued on next page.)

OTHER PUBLICATIONS

Fabric Filter Bag Leak Detection Guidance, author unknown, EPA, Sep. 97.*

(List continued on next page.)

*Primary Examiner*—Hezron Williams
*Assistant Examiner*—David A. Rogers
(74) *Attorney, Agent, or Firm*—Baker & Daniels

(57) ABSTRACT

A safety vacuum cleaner including a measuring system for residual dust monitoring, including a housing having an air passage with an inlet, an outlet, and a flow cross section. A turbine is disposed within the air passage and is rotatable to move an air stream through the air passage, the air stream containing dust particles. The turbine is electrically grounded such that electrical charges associated with the particles are removed upon contact of the particles with the turbine. A filter element is disposed within the air passage, and at least one electrode is disposed within the air passage downstream of the turbine, the electrode shaped as a grid covering the flow cross section of the air passage. The electrode conducts an electrical current responsive to contact with uncharged particles and emits a measurement signal indicative of the amount of the particles in the air stream.

11 Claims, 2 Drawing Sheets

U.S. PATENT DOCUMENTS

| | | | | |
|---|---|---|---|---|
| 5,330,559 | A | * | 7/1994 | Cheney et al. .................. 95/63 |
| 5,400,465 | A | * | 3/1995 | Bosses et al. .................. 15/339 |
| 5,542,146 | A | * | 8/1996 | Hoekstra et al. ............... 15/319 |
| 5,591,895 | A | * | 1/1997 | Rigby ........................ 73/28.01 |
| 5,644,241 | A | * | 7/1997 | Hewelt ........................ 324/454 |
| 6,192,740 | B1 | * | 2/2001 | Thomas et al. ............ 73/28.01 |
| 6,395,073 | B1 | * | 5/2002 | Dauber ........................ 96/134 |
| 6,571,422 | B1 | * | 6/2003 | Gordon et al. ................ 15/339 |
| 2002/0042965 | A1 | * | 4/2002 | Salem et al. .................. 15/339 |
| 2002/0134238 | A1 | * | 9/2002 | Conrad et al. ................. 95/79 |

FOREIGN PATENT DOCUMENTS

| | | | | |
|---|---|---|---|---|
| EP | 870462 A1 | * | 10/1998 | ............. A47L/9/19 |
| GB | 2 225 933 | | 6/1990 | |
| JP | 01153131 | | 6/1989 | |
| JP | 03280915 | | 12/1991 | |
| JP | 03280915 A | * | 12/1991 | ............. A47L/9/28 |
| JP | 04063153 | | 2/1992 | |
| WO | WO 94/23281 | | 10/1994 | |
| WO | WO 94/25865 | | 11/1994 | |

OTHER PUBLICATIONS

Wagon Creating Charges With Friction, Science, 1999.*

Ramsey, The Emergence of Triboelectric Technology, Polution Engineering, Sep. 98.*

Search Report dated Sep. 8, 1999, Application No. 199 00 484.6.

Office Action dated Jan. 26, 2001, with cited references, Application No. 199 00 484.6.

* cited by examiner

MEASURING SYSTEM FOR THE CONTROL OF RESIDUAL DUST IN SAFETY VACUUM CLEANERS

The invention relates to a measuring system for the monitoring of residual dust for safety vacuum cleaners.

Similar measuring arrangements for the monitoring of the dust concentration in the exhaust air in vacuum cleaners are already known and these employ physical measuring principles such as, for example, the measurement of the differential pressure or of the radiation reflection.

In differential pressure measurement the cc prevailing pressure before the filter unit is compared with the prevailing pressure after the filter unit or after the motor, the differential pressure not being allowed to pass below a threshold value. With a non-defective and unfouled filter the admissible differential pressure is least, the differential pressure increases with increasing blockage of the filter. If the filter cracks, then an inadmissible pressure balance between the chambers before and after the filter arises and the differential pressure falls below the admissible threshold value in the direction of zero differential pressure. The undershooting of the differential pressure with a cracked filter, but also the exceeding of the differential pressure with a blocked filter, can be used as alarm means for purposes of the motor control.

A disadvantage in the measuring principle with the differential pressure method is that the pressure fluctuations, caused by running fluctuations of the motor because of changing volumes and speeds of the suction medium and by differing blocking and quality of the filter, are nevertheless so high that an exact registration of the undershooting or exceeding of the threshold value can be achieved only inadequately especially in the case of low differential pressures.

DE-GM 92 09 407.4 discloses a detection device of filter breakage in vacuum cleaner arrangements, which device uses the principle of infrared radiation reflection for the particle measurement in the exhaust air. In the exhaust air channel of a vacuum cleaner arrangement there are arranged an infrared sender and an appertaining infrared receiver angularly offset to one another on the circumference of the exhaust air channel, long-wave energy being radiated into the exhaust air channel by the infrared sender. This infrared radiation is then partly reflected on the dirt particles flowing through in such manner that the reflection radiation is registered over the infrared receiver offset, for example, by 90° to the infrared sender.

The energy supplying and the measuring signal preparation occurs in an evaluating electronic system connected with the sender and receiver. The measuring field is defined by the overlapping of the respective input and output jet cone.

On concentration rise of the dust particles in the exhaust air channel the IR energy irradiated by the sender is reflected (amplified) on the particles and measured in the receiver and in this manner a threshold value preset in the evaluating electronic system can be overstepped, which threshold value triggers an alarm and/or brings the motor to a standstill. In this manner, a filter breakage is measured and displayed, in order to avoid health-threatening particle emissions into the environmental air, by manual or automatic switching off of the suction motor, and to make possible a filter change in proper time.

A disadvantage in the measuring principle with infrared radiation reflection for the residual dust particle measurement is that the optical system can be very easily soiled, both that of the IR sender and also that of the IR receiver, whereby the measurement signal is falsified, since the dust particles on sender and receiver likewise absorb and reflect IR energy; these dirt particles, however, are not to be measured, since, after all, they do not reflect the actual flow state in the exhaust air channel. This falsification of the measurement signal by fouling can be poorly compensated, since the degree of fouling is constant neither in time nor locally, and therewith cannot be exactly defined. Thereby for an effective measurement, whether technical and/or computational, compensation is possible only very defectively.

A further disadvantage of the measuring principle with infrared radiation reflection for residual dust particle measurement is that measurement is restricted to the focusing range of the sender/receiver, i.e., the measurement field defined by the overlapping of the radiation cones of sender and receiver does not cover the entire cross-section of the outlet tube, whereby outside of the measuring field no particle measurement takes place, which likewise leads to an undefined, poorly compensatable falsification of the measurement signal.

The purpose for this invention, therefore, is to provide a measuring system for residual dust monitoring in safety vacuum cleaners in such manner that the above-mentioned disadvantages of the state of the art are reduced or even eliminated. Specifically, it is found that the measuring system is more sturdy resulting in a more dependable construction. It is also found that the system provides more accurate measurements in the case of low particle concentration in the exhaust air.

Here the measuring system, on the one hand, is to be less subject to fouling and therewith to make possible longer maintenance intervals; on the other hand, it is also meant to make possible a more accurate measurement of the particle concentration in the exhaust air, in order to give more exact information about the state of the filter, as to whether a defect is present or not. It is also to make it possible to determine low dust concentrations in the exhaust air.

For the solution of the problem posed there serves the technical teaching of the present invention.

An essential feature is that, according to the invention, the measuring system of the residual dust monitoring in safety vacuum cleaners provides for at least one measuring electrode mounted upstream behind the filter unit. The measuring element transmits a current signal to a measurement value processing unit. The current signal is produced by contact tension between measuring electrode and particles and depends on the particle concentration.

There arises here a contact voltage through intensive contact of the dust particles carried along in the carrier medium (air) with the material of the measuring electrode. If the dust particles consist of a material which is materially different from the material of the measuring electrode, then there occurs a passing-over of electrons which flow off to the lower potential as a function of the contacting particles and therewith of the particle concentration in the exhaust air. This holds for both electrically conducting particles and electrically insulating particles. With electrically conducting particles the cause of the charge separation lies in the differing emergence work in comparison to the measuring electrode, and with electrically insulating particles the charge separation lies in the different electron affinity in comparison to the measuring electrodes.

In a preferred form of execution of the measuring system for residual dust monitoring for safety vacuum cleaners according to the invention, it is provided that at least one measuring electrode is arranged downstream within the outlet tube behind the filter and behind the turbine, preferably in the end zone of the outlet tube. Also, it must be possible to arrange the measuring electrode in the vicinity of the turbine in the outlet tube or in the motor block of the turbine itself.

In a further form of execution of the inventive measuring system of the residual dust monitoring in safety vacuum cleaners it is provided that at least one measuring electrode is mounted downstream behind the filter or in front of the turbine, preferably directly on or in the near zone of the filter outlet surface. The measuring electrode can, however, also be arranged in an intermediate tube or an intermediate chamber between filter and turbine or else in the vicinity of the turbine in the motor block.

It is preferred that the measuring electrode cover the entire flow cross-section, but in such manner that the flow resistance in the safety vacuum cleaner is only inappreciably increased and thus the efficiency of the vacuum cleaner is not impaired by the measuring arrangement.

Preferably, therefore, at least one measuring electrode covers the entire filter output surface, the cross-section of the intermediate tube, or the intermediate chamber between filter and turbine, or the entire cross-section of the outlet tube.

In a preferred form of execution the measuring electrode is constructed in grid form, similar to a mesh wire or perforated plate, and it lies with its mantle surface firmly on the inner circumference of the tube or of the chamber.

The grid-form measuring electrode can be bounded by an annular element around the mantle surface, in which case preferably the annular element consists of the same material as the measuring electrode. It can, however, also consist of flexible plastic, into which the measuring electrode is cast and is thrust with clamping effect into the outlet tube. The fixing into position of the measuring electrode can occur over a releasable or unreleasable connection. It is preferred, however, that the fixing is over a releasable screw, a rest or clamping connection, or a welding connection.

If the measuring electrode lies directly on the filter outlet surface or in its vicinity, then it has about the same form as the filter. Therefore, for example, a cylindrical/tubular form or disk form can be joined with the filter on its face side and/or mantle surface.

Several grid-type measuring electrodes can be provided, which again transmit their measuring signal to a measuring value processor. Here there can also be measured information about the level of the particle concentration, the distribution of the particle concentration over the cross-section of the outlet tube, and therewith the position of the filter defect can be determined. This holds, of course, only for a measuring electrode that is located between filter and turbine, since the particles in the turbine substantially change their flow path, so that a correlation between measuring point and particle concentration behind the turbine or also in the vicinity in front of it is no longer possible.

Through the fact that the dust particles can be charged in a certain manner before their contact with the measuring electrode already in the inlet channel, in the dust chamber (housing), in their passage through the filter and the turbine and in the outlet channel, the dust particles are preferably discharged before contact with the measuring electrode in order to minimize measurement value falsifications.

This takes place by grounding of the parts of the safety vacuum cleaner which first come in contact with the particles before the latter encounter the measuring electrode.

As a rule a grounding of the turbine housing suffices which with low protection demands is directly grounded, and in the case of high protective requirements is laid on artificial ground, therefore over protective impedances with one of the phases, or is electrically conductively connected with one of the phases or with the zero conductor of the turbine motor.

It is also possible, instead of this or additionally, to ground the housing of the safety vacuum cleaner, which is mostly standardly provided also for operator safety reasons when the housing is not insulatingly constructed.

Under the above-mentioned protection requirements there are to be understood contact and foreign-body protection, water protection and explosion protection, in which context there fall under explosion protection both the use of the apparatus in a danger zone (for example tank location zone), and also the use of the apparatus with hazardous substances (for example drawing-off of explosive gases and fluids).

Since the electrical currents to be measured in the measuring electrode, by reason of the contact voltage through intensive contact of the dust particles carried along in the carrier medium (air) with the material of the measuring electrode, amount merely to a few nano-amperes (nA, $10^{-9}$), for the further processing of the measuring signal, this signal must first be amplified.

Here a differential amplification offers itself, for example over a linear, inverting, differentiating operation amplifier, which inverts the measuring signal and amplifies it in respect to potential ground or artificial ground, correspondingly into the milli-ampere range (mA, $10^{-3}$).

Of course all possible constructions of an operation amplifier can be provided, such as adders, substracters, integraters, differentiators and all combinations of these, depending on what is to be measured and how the reckoning is to be performed.

It is obvious that this operation amplifier is preferably accommodated in a microchip and/or on a microprocessor which, for example, also fulfills still other assignments, such as, forexample the turbine regulation or other measuring, controlling and regulating assignments. It is possible, for example, for corresponding measurement values or indications to be issued on displays on the apparatus or only in case of disturbance.

This operation amplifier, microchip or microprocessor can then be connected over a usual interface with a personal computer or another data processing apparatus in order to coordinate measuring, control and regulating problems or in order to read out from the storage unit of the microchip or of the microprocessor, for example for statistical purposes. There can also occur a calibration over the PC, in which the threshold values for the further processing of the measurement signal are input, such as for example triggering of the alarm or switching on and off of the turbine.

If the filter unit is defective (for example burst or torn), then the particle concentration in the exhaust air stream rises rapidly and many more particles contact the measuring electrode and therewith the current flow rises away from the measuring electrode, and therewith the evaluating unit engaged on outlet side in the amplifier stage. Here then the measured value (actual value) is compared with the Oat threshold value (desired value) and then an optical and/or acoustic alarm signal is given. In addition to this or as a replacement for this the turbine motor can be switched off automatically, which must be accomplished manually in the case of the exclusive optical and/or acoustic alarm signal.

The present invention is intended to detect an ever so slight filter leakage, but this measuring arrangement can also be used to detect, to display the blocking of the filter, to trigger optical or acoustic alarm, to turn off turbines automatically or by hand, or to modify the action of the suction stream on them, or to change filters automatically or by hand. If, therefore, the filter is blocked, then a predetermined threshold value of the measuring signal is undershot and again and optical and/or acoustic alarm signal can be given or the turbine motor can be shut off. In distinction to the turbine standstill, in which measurement signal is registered, with blocked filter and switched-on turbine a slight particle concentration is still measurable.

In forms of execution of the safety vacuum cleaner with several independent filter units, by the exceeding of the preset threshold value internally and automatically, the suction medium can be led to another turbine with unused/ nondefective filter unit and it is not until the last unused/ nondefective filter is likewise used-up that an alarm is given.

In the forms of execution of the safety vacuum cleaner with several independent turbines, by the exceeding of the preset threshold value internally and automatically the suction medium can be led to another turbine with unused/ nondefective filter unit and it is not until the last unused/ nondefective filter is likewise used-up that an alarm is given.

For the reduction of disagreeable or health-harmful noises through the grid-form measuring electrode in the flow channel, it can be provided that in the region of the outlet channel a sound damper is provided, which influences the sound vibrations in such manner that the noise level is lowered below an admissible degree. Preferably the arrangement of the sound damper is made downstream at the free end of the outlet channel.

The inventive object of the present invention is yielded not only for the object of the individual patent claims, but also from the combination of the individual patent claims among one another.

All the indications and features disclosed in the documents, inclusive of the abstract, in particular the spatial formation represented in the drawings, are claimed as CA, essential to the invention insofar as they are novel individually or in combination with respect to the state of the art.

In the following the invention is explained in detail with the aid of drawings representing only one course of execution. Here there proceed from the drawings and their description further inventively essential features and advantages of the invention.

Figure 1:
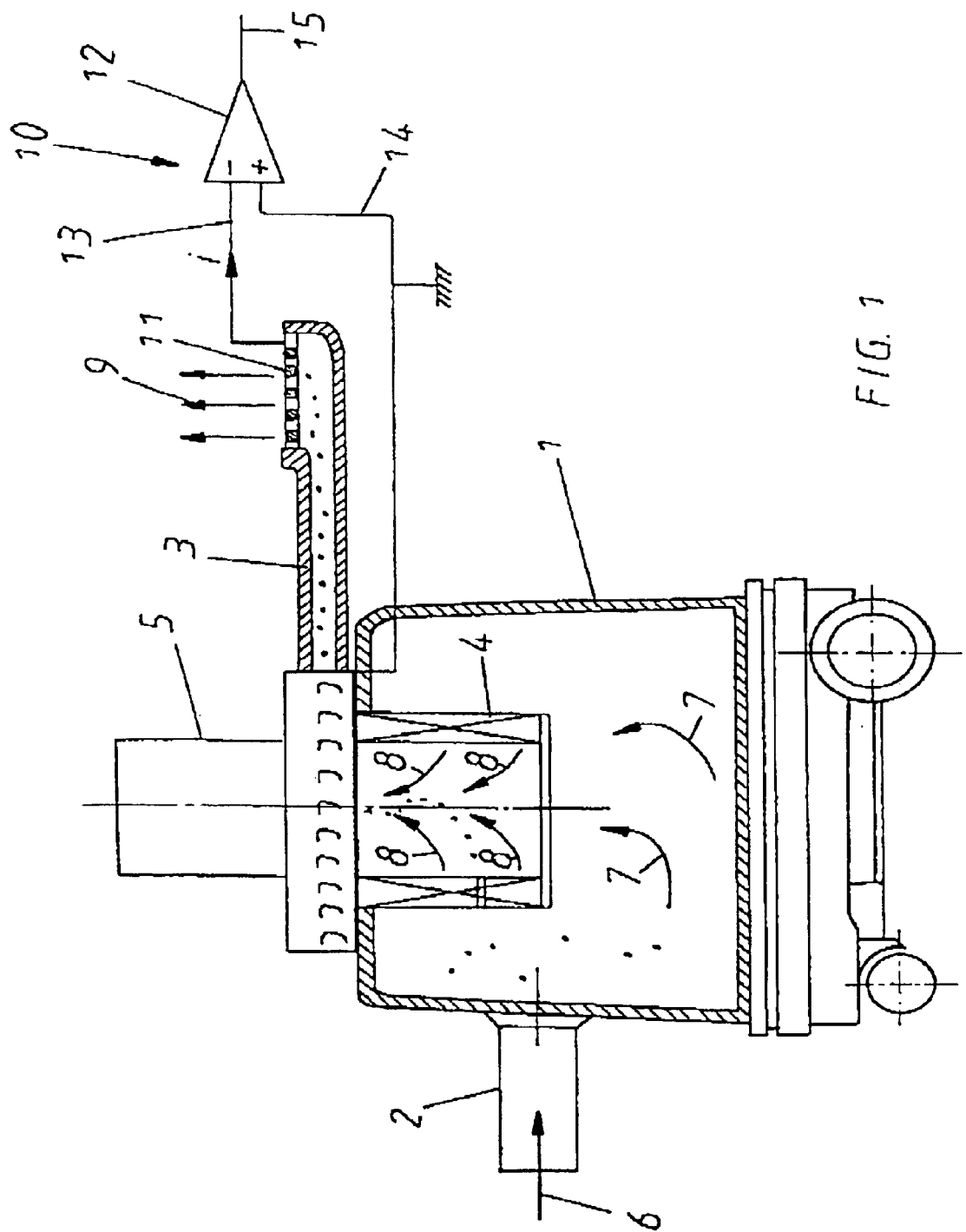
FIG. 1 shows the measuring system according to the invention for the residual dust monitoring for safety vacuum cleaners with schematic electrical wiring. Here the upper part of the safety vacuum cleaner is represented in section and the grid-form measuring electrode is mounted in the free end of the outlet channel.

In FIG. 1 the measuring system of the invention for residual dust monitoring in safety vacuum cleaners is drawn exclusively schematically as a block circuit diagram, in order to explain the electrical wiring of the measuring electrode 11 and the manner of function of the entire safety vacuum cleaner in conjunction with the measuring system 10. It is obvious that the electronic components 12 of the measuring system 10 are mounted in a separate module or on the housing 1 of the safety vacuum cleaner, which module is HF-protected. The measuring electrode 11 itself is arranged here, representative of all other forms of execution, in the free end of the outlet channel 3. The turbine 5 with downstream-emplaced, rotationally symmetrical filter element 4 is sealed off on the housing 1 of the safety vacuum cleaner, the upper part of which is represented here in section.

By operating of the turbine 5 now through the inlet channel 2 in flow direction 6 the medium to be drawn off (for example dust-containing air) is drawn into the interior of the housing 1. There the heaver drawn-in dust particles fall to the bottom and the lighter ones are carried along in flow directions 7 in the direction of the filter element 4.

Depending on pore size of the filter 4, then again larger particles are held back before or within the filter 4, while smaller particles below the pore size of the filter 4 force their way preferably through the mantle surface of the filter 4 and are then drawn in the flow direction 8 in the direction of turbine blade 5.

In the turbine 5 the particles are then conveyed in the direction of the outlet channel 3, pass the zone of the measuring electrode and leave again the safety vacuum cleaner in flow direction 9. In the normal case with unblocked and nondefective filter 4 only the smallest particles (depending on pore size of filter 4) emerge from the safety vacuum cleaner. With a defective filter 4 undesirably many particles in all orders of magnitude (depending on defect) emerge from the safety vacuum cleaner. With a blocked filter 4 virtually no particles emerge from the safety vacuum cleaner.

On contact of the particles with the grid-form measuring electrode, which extends over the entire cross-section of the outlet channel, the effect of the charge separation sets in as explained above, and over the measuring electrode there flows a measuring current stream in the direction of the evaluating unit. This measuring current rises with increasing number of contacts of the particles with the grid-form measuring electrode and thus the measuring current reflects very accurately the number of particles in the exhaust air. By the homogeneous distribution of the grid-form measuring electrode over the entire cross-section of the outlet channel there is achieved a statistical averaging and accordingly the number of particles can be determined very accurately after a single calibration of the measuring system, although many of the particles, of course, pass through the measuring electrode without contact.

The calibration occurs over a predefined number of particles of medium size (depending on pore size of the filter) which is brought into correlation with the off-flowing measuring current from the measuring electrode.

Since the measuring currents are only very small (a few nA), these must first be fed over an entry line 13, for example to a differential amplifier 12 and amplified to several mA in order to give a signal to a further evaluating unit. The second entry line 12 is connected here with the turbine housing 5 and lies on ground there or on artificial ground, depending on grounding of the turbine housing 5.

This signal can indicate, for example optically or acoustically, whether a preset threshold value is exceeded, or whether it is undershot by blocking of the filter 4. It is also possible by this signal for a setting magnitude to be given directly from the evaluating unit and, for example, for the turbine 5 to be stopped and/or the filter 4 to be changed automatically in the housing 1.

A measurement of the particle number can also occur continuously, in order then to use these measurement values statistically in an evaluating unit or a microprocessor and/or computer connected thereto.

These measurement values can then give information, for example, as to how rapidly and in what manner the filters 4 are blocked and/or become defective. Also through such statistics, for example, a production process can be replicated and/or monitored, in which dust-containing production wastes are drawn off. There can also be established, for example, a mathematical relation between tool and/or tool parameters with the concentration course of the particles over the time and/or place.

Figure 2:
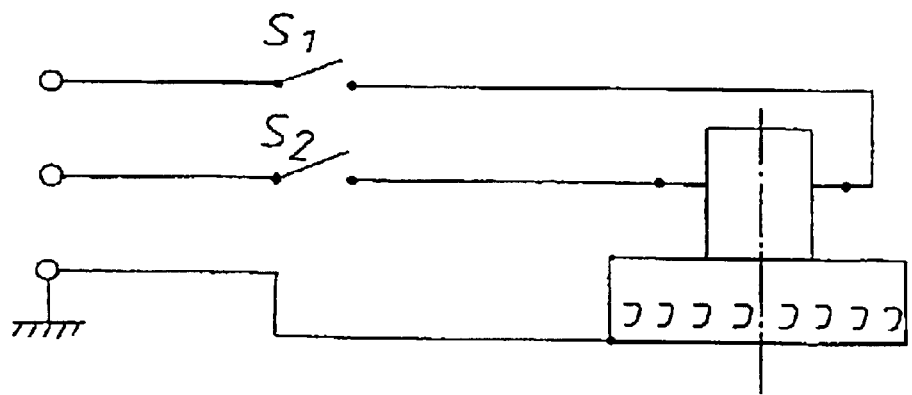
FIG. 2 shows a first switching principle of the grounding of the turbine for low protection requirements.

FIG. 2 shows a first switching principle for the grounding of the turbine for low protective demands, in which the housing of the turbine is grounded there, and the drive is represented schematically over phases and zero conductors and the switches $S_{1,1}$ present therein.

Figure 3:
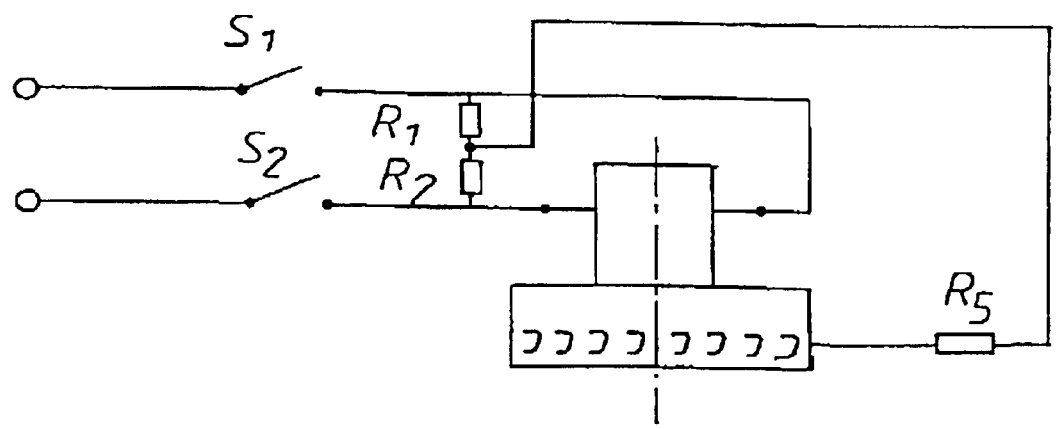
FIG. 3 shows a second switching principle of the grounding of the turbine for increased protection requirements in the form of an artificial grounding.

FIG. 3 shows a second switching principle of the grounding of the turbine 5 for increased protective demands in the form of an artificial grounding, in which the housing of the turbine 5 is connected over a protective resistor R and in each case at least one further resistance $R_1$, $R_2$ with the phases and the zero conductor of the power supply of the turbine 5. The potential of the artificial grounding, therefore, depending on the relation of the resistances $R_1$, $R_2$ and of the voltage divider, lies between the potential of the phase and the potential of the zero conductor.

Drawing Leagend

1 Housing of the safety vacuum cleaner
2 Inlet channel
3 Outlet channel
4 Filter element
5 Turbine
6 Flow direction
7 Flow direction
8 Flow direction
9 Flow direction
10 Measuring system
11 Measuring electrode
12 Differential amplifier
13 Input line
14 Input line
15 Output line
$R_1$ Resistance
$R_2$ Resistance
$S_1$ Switch
$S_2$ Switch

What is claimed is:

1. A safety vacuum cleaner including a measuring system for residual dust monitoring, comprising:

a housing including an air passage having an inlet, an outlet, and a flow cross section;

a turbine at least partially disposed within said air passage, said turbine rotatable to move an air stream through said air passage, the air stream containing dust particles, said turbine electrically grounded such that electrical charges associated with the particles are removed upon contact of the particles with said turbine;

a filter element disposed within said air passage; and at least one electrode disposed within said air passage downstream of said turbine, said electrode shaped as a grid covering said flow cross section of said air passage, said electrode conducting an electrical current responsive to contact with uncharged particles and emitting a measurement signal indicative of the amount of the particles in the air stream.

2. The vacuum cleaner of claim 1, wherein said outlet comprises an outlet tube having an open end portion, said electrode positioned within said open end portion.

3. The vacuum cleaner of claim 1, wherein said electrode is mounted within said air passage proximate said turbine.

4. The vacuum cleaner of claim 1, wherein said turbine includes at least one turbine blade disposed within a turbine housing, said electrode mounted within said turbine housing proximate said at least one turbine blade.

5. The vacuum cleaner of claim 1, wherein all portions of said air passage, besides said electrode, are one of directly and artificially grounded.

6. The vacuum cleaner of claim 1, further comprising a differential amplifier and a processing unit, said differential amplifier amplifying said measurement signal and conducting said measurement signal to said processing unit.

7. The vacuum cleaner of claim 6, wherein said processing unit carries out beatwise a comparison of said measurement signal with a desired value, said processing unit delivering an output signal when said measurement signal undershoots or exceeds said desired value.

8. The vacuum cleaner of claim 7, wherein said output signal results in one or more of the following:

one of an optical and an acoustic alarm is given;

said turbine is switched off;

said filter element is changed; and a second turbine and filter are activated.

9. The vacuum cleaner of claim 6, wherein said processing unit is interfaced with one of an external data processing installation and a computer.

10. The vacuum cleaner of claim 1, wherein said measurement signal is shown on a display, said displayed measurement signal corresponding to one or more of the following:

a direct measurement signal;

a correlating particle number;

a proportional filter blocking; and a degree of filter damage.

11. The vacuum cleaner of claim 1, further comprising a storage unit, said storage unit receiving and storing said measurement signal.

* * * * *